United States Patent [19]

Nakahara et al.

[11] 4,418,196

[45] Nov. 29, 1983

[54] PROCESS FOR PREPARING TRIACETONE AMINE

[75] Inventors: Yutaka Nakahara, Iwatsuki; Naohiro Kubota, Ageo; Bunji Hirai, Kuki; Tohru Haruna, Okegawa, all of Japan

[73] Assignee: Adeka Argus Chemical Co., Ltd., Urawa, Japan

[21] Appl. No.: 410,239

[22] Filed: Aug. 23, 1982

[30] Foreign Application Priority Data

Sep. 16, 1981 [JP] Japan ................................ 56-145771

[51] Int. Cl.$^3$ .......................................... C07D 211/74
[52] U.S. Cl. .................................................. 546/242
[58] Field of Search ...................................... 546/242

[56] References Cited

U.S. PATENT DOCUMENTS 3,513,170 5/1970 Murayama et al. ................. 546/242
4,252,958 2/1981 Hirai .................................... 546/242

FOREIGN PATENT DOCUMENTS 13865 8/1980 European Pat. Off. ............ 546/242
2916471 11/1980 Fed. Rep. of Germany ...... 546/242
3,013,403 10/1981 Fed. Rep. of Germany ...... 546/242

Primary Examiner—Norma S. Milestone

[57] ABSTRACT

A process is provided for preparing triacetone amine (2,2,6,6-tetramethyl-4-oxo piperidine) by reacting acetone and/or an acid condensate of acetone with ammonia in the presence of at least one catalyst selected from the group consisting of organotin halides, 1,3,5,2,4,6-triazatriphosphorin hexahalides and cyanuric halides.

16 Claims, No Drawings

PROCESS FOR PREPARING TRIACETONE AMINE

Triacetone amine (2,2,6,6-tetramethyl-4-oxopiperidine) has the structure

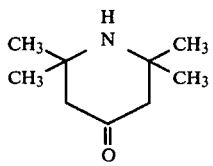

and is useful as an intermediate in the preparation of piperidyl light stabilizers and drugs.

In the reaction of acetone with ammonia the ammonia first acts as a base, inducing aldol condensations of two and three molecules of acetone to form mesityl oxide and phorone, respectively. These react with a molecule of ammonia to form diacetone amine (I) and triacetone amine (II).

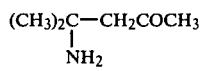

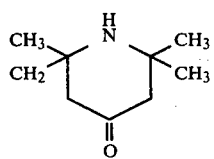

Ammonia adds to an olefinic linkage when that linkage is alpha, beta to a carbonyl group. The mechanism is probably 1:4 addition, followed by "ketonization":

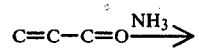

W. Heinz *Annalen der Chemie* 203 336 (1880) discloses the reaction of phorone with ammonia.

In the case of phorone, the addition of $NH_3$ would give $(CH_3)_2C(NH_2)CH_2COCH=C(CH_3)_2$ in which the $NH_2$ and the farther olefinic carbon are in the 1:6 position. Intramolecular addition then takes place to form triacetone amine.

H. K. Hall *J Am Chem Soc* 79 5447 (1957) describes the reaction of acetone with ammonia in the presence of calcium chloride.

Into a mixture of acetone and $CaCl_2$ was passed ammonia for 30 minutes. More ammonia was introduced for 15-minute periods at intervals of 3 hours for 5 days. The mixture was allowed to stand at room temperature an additional 4 days. At this time it was sirupy and dark, but the calcium chloride had not liquefied. It was poured into 50% NaOH (when the liquid was merely decanted from the solids the yield was much lower). The upper layer was decanted from the heavy white sludge of calcium hydroxide, which was then rinsed with ether until tests with ethereal picric acid indicated the absence of amines in the extract. The combined ether layers were dried over $K_2CO_3$ and distilled to give a yellow liquid; careful fractionation of this material through a spinning band column gave 666 g (20.0%) triacetone amine, b.p. 102°–105° (18 mm), m.p. 34°–36° (lit. m.p. 36°). Wolff-Kishner reduction of this material gave a minimum yield of 59.7% of 2,2,6,6-tetramethyl piperidine, b.p. 151°–159°.

Murayama U.S. Pat. No. 3,513,170 discloses the conversion of 2,2,4,4,6-pentamethyl-2,3,4,5-tetrahydropyrimidine(acetonine) to triacetone amine by the action of a Lewis acid in the presence of water.

These processes mentioned are unsatisfactory because of the low yields and long reaction times.

Orban U.S. Pat. No. 3,959,295 discloses the preparation of triacetone amine from acetone and ammonia in the presence of acidic catalysts in two stages carried out at two different temperatures, about 15° C. in the first stage, and from 50° to 55° C. in the second stage.

The yield of triacetone amine is rather low, however.

In accordance with this invention, triacetone amine is prepared by reaction of an acetone compound with ammonia in the presence of a catalytically effective amount of a compound selected from the group consisting of organotin halides, 1,3,5,2,4,6-triaza-triphosphorin hexahalides, and cyanuric halides.

The acetone compound employed as a starting material can be acetone or a condensation product of acetone with itself, such as diacetone alcohol, mesityl oxide, or phorone.

The organotin halide catalysts of this invention have the structure $$R_nSnX_{4-n}$$

in which

R is a hydrocarbon group selected from the group consisting of aliphatic and cycloaliphatic hydrocarbon groups and such groups including oxy and ester groups in the chain;

X is halogen; and n is 1, 2 or 3.

The halogen can be chlorine, bromine or iodine.

The aliphatic hydrocarbon and oxyhydrocarbon and carboxylic ester hydrocarbon groups have from one to about ten carbon atoms. The cycloaliphatic hydrocarbon and oxyhydrocarbon and carboxylic ester hydrocarbon groups have from five to about ten carbon atoms.

Exemplary are methyl, ethyl, propyl, isopropyl, butyl, isobutyl, tert-butyl, sec-butyl, amyl, isoamyl, hexyl, octyl and decyl; cyclopentyl, cyclohexyl, cycloheptyl and cyclooctyl; oxymethyl, oxyethyl, oxypropyl, oxybutyl, oxyisobutyl, oxyhexyl, oxyoctyl and oxydecyl; ethylene oxyethyl, ethylene oxybutyl, di(ethyleneoxy)ethyl, butylene oxybutyl, and tri(ethyleneoxy)ethyl; methylene carboxyethyl, ethylene carboxyethyl, butylene carboxybutyl, hexylene carboxymethyl and octylene carboxymethyl.

Typical organotin halides include monomethyltin trichloride, monomethyltin tribromide, monomethyltin triiodide, dimethyltin dichloride, dimethyltin bromide, dimethyltin diiodide, trimethyltin chloride, monobutyltin trichloride, monobutyltin tribromide, monobutyltin triiodide, dibutyltin dichloride, dibutyltin dibromide, dibutyltin diiodide, tributyltin chloride, monooctyltin trichloride, dioctyltin dichloride, trioctyltin chloride, cyclopentyltin trichloride, cyclohexyltin trichloride, dicyclohexyltin dibromide, tricyclohexyltin chloride, dicycloheptyltin dichloride, cycloheptyltin triiodide, cyclooctyltin tribromide, mono(methoxy carbonylethyl)tin trichloride, di(methoxy carbonylethyl)tin dichloride, mono(butoxy carbonylethyl)tin trichloride, and di(butoxycarbonylethyl)tin dichloride.

The 1,3,5,2,4,6-triaza-triphosphorinhexahalides have the formula

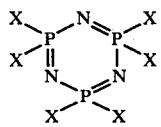

wherein X is halogen, chlorine, bromine or iodine.

Exemplary are the hexachloride, the hexabromide and the hexaiodide.

The cyanuric halides have the formula:

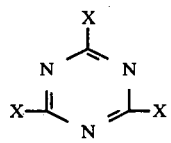

wherein X is halogen, chlorine, bromine or iodine.

Exemplary are cyanuric chloride, cyanuric bromide and cyanuric iodide.

The chlorine compounds are the most effective catalysts, and therefore are preferred, in all three of the above classes. Only a small amount of catalyst is effective. As little as 0.01% by weight of the acetone compound can be used. A preferred range is from about 0.05% to about 10% by weight of the acetone compound.

A number of materials function as co-catalysts when combined with the catalyst of this invention, interacting beneficially to give synergistic results, better than with either alone. Co-catalysts that can be used with the catalyst of this invention include elemental bromine and elemental iodine; lithium, sodium and potassium bromide and iodide; ammonium chloride, bromide and iodide; hydrazine chloride; lithium and ammonium thiocyanate; maleic hydrazide, barium hydroxide; synthetic absorbents such as magnesium silicate hydrate and aluminum silicate hydrate; boron trifluoride, zinc chloride, and calcium chloride.

When a co-catalyst is used together with the catalyst of this invention, the amount of co-catalyst is usually within the range from about 0.01 to about 10% by weight of the acetone compound, preferably from 0.1 to 5%.

The relative proportions of acetone compound and ammonia can be varied over a wide range. The molar ratio of acetone to ammonia can be within the range from about 1:1 to about 20:1, preferably from 2:1 to 10:1.

The reactants, catalyst, co-catalyst when used, solvent and so on can be charged all at once or in several portions as the reaction proceeds.

Neither reaction temperature nor reaction pressure is critical. The process of the invention will proceed at room temperature or below, as well as at elevated temperatures. Preferably, the reaction temperature is within the range from about 0° C. and the boiling point of the reaction mixture at atmospheric pressure, with a range of from 30° to 60° C. particularly preferred. If the reaction mixture boils at 60° C. or below, the reaction temperature can be increased to from 60° to 110° C. by applying superatmospheric pressure up to 30 atmospheres, preferably up to 5 atmospheres.

The required reaction time ranges from about 3 to about 30 hours, in inverse relationship to the reaction temperature.

A solvent or diluent is not necessary in the process of this invention but one can be used, if desired. The solvent should be inert, and have a boiling temperature at or above the selected reaction temperature. Solvent that can be used, for example, are aliphatic hydrocarbons, such as pentane, hexane, heptane; aromatic hydrocarbons such as benzene, toluene, xylene; chlorinated aliphatic and aromatic hydrocarbons such as methylene chloride, trichloroethane, chloroform, carbon tetrachloride; chlorobenzene, the dichlorobenzenes and trichlorobenzenes; the chlorotoluenes and the chloroxylenes; aliphatic and cycloaliphatic alcohols such as methanol, ethanol, isopropanol, butanol, t-butanol, 2-ethylhexanol, cyclohexanol; aliphatic and heterocyclic ethers such as diethyl ether, tetrahydrofuran and dioxane.

In the preparation of triacetone amine according to the process of this invention, water does not interfere. It is not necessary to add any water, nor to take pains to exclude it. Some water is formed as a product of the reaction between acetone and ammonia; such water can be removed as it forms, or allowed to accumulate and become part of the solvent system.

At the end of the reaction, the lowest boiling components of the mixture are unreacted acetone, water, and solvent, if used; these can be stripped off and used as the solvent or diluent in subsequent preparations without separation from one another. Triacetone amine can be recovered from the reaction mixture by conventional techniques, for example by precipitation as the hydrate by adding water; or by precipitation as the hydrohalide, sulfate or oxalate salt by adding the appropriate acid; or by distillation, suitably after adding an excess of strong alkali, such as concentrated aqueous potassium or sodium hydroxide solution.

The following Examples represent preferred embodiments of the invention.

EXAMPLES 1 TO 5

A flask equipped with a Dimroth condenser and a gas inlet tube was charged with acetone 180 g, methanol 9 g, the catalyst shown in Table I 1.8 g. Ammonia gas was then introduced over 5 hours at 15° to 20° C. while stirring. Then, the flow of ammonia gas was stopped, and the mixture was heated at 50° to 55° C. for 15 hours.

At the end of this time, the reaction mixture was stripped in vacuo, and the triacetone amine recovered by vacuum distillation. The results are shown in Table I.

TABLE I

| Example No. | Catalyst | Yield of Triacetone amine | |
|---|---|---|---|
| | | (g) | %* |
| Control 1 | Ammonium chloride | 31.9 | 20 |
| Control 2 | Stannic chloride | 25.5 | 16 |
| Example 1 | Dimethyltin dichloride | 57.3 | 36 |
| Example 2 | Dibutyltin dichloride | 52.7 | 33 |
| Example 3 | Monooctyltin trichloride | 54.2 | 34 |
| Example 4 | Cyanuric chloride | 62.2 | 39 |
| Example 5 | 1,3,5,2,4,6-Triaza-triphosphorin | 51.4 | 32 |

TABLE I-continued

| Example No. | Catalyst | Yield of Triacetone amine (g) | %* |
|---|---|---|---|
| | hexachloride | | |

*Based on acetone used.

The improvement in yield when the catalyst of the invention is used is apparent from the data.

EXAMPLES 6 TO 11

Into a mixture of 50 g acetone and 2.7 g of the catalyst shown in Table II was introduced ammonia gas for 4 hours at 15° to 20° C., with stirring. 130 g Acetone then was added, and the reaction mixture stirred for 15 hours at 50° to 55° C. The reaction mixture was worked up by distillation in the same procedure as in Examples 1 to 5. The results are shown in Table II.

TABLE II

| Example No. | Catalyst | Yield of Triacetone amine (g) | %* |
|---|---|---|---|
| Control 1 | Ammonium chloride | 52.9 | 33 |
| Control 2 | Stannic chloride | 38.2 | 24 |
| Control 3 | Calcium chloride | 14.7 | 9 |
| Example 6 | Monomethyltin trichloride | 70.1 | 44 |
| Example 7 | Dimethyltin dichloride | 73.5 | 46 |
| Example 8 | Dibutyltin dichloride | 67.0 | 42 |
| Example 9 | Mono(butoxycarbonylethyl) tin trichloride | 63.9 | 39 |
| Example 10 | Cyanuric chloride | 76.5 | 48 |
| Example 11 | 1,3,5,2,4,6-Triazatriphosphorin hexachloride | 68.6 | 43 |

*Based on acetone used.

The improvement in yield when using the catalyst of the invention is apparent from the data.

EXAMPLES 12 TO 15

An autoclave was charged with 290 g of acetone, 17 g of ammonia gas and 2.9 g of the catalyst shown in Table III. Then, the mixture was allowed to react for 7 hours at 70° C., while stirring. The reaction mixture was worked up as in Examples 1 to 5. The results are shown in Table III.

TABLE III

| Example No. | Catalyst | Yield of Triacetone amine (g) | %* |
|---|---|---|---|
| Control 1 | Ammonium chloride | 35.7 | 23 |
| Control 2 | Zinc chloride | 18.3 | 12 |
| Example 12 | Dimethyltin chloride | 71.5 | 46 |
| Example 13 | Monobutyltin chloride | 66.4 | 43 |
| Example 14 | Cyanuric chloride | 79.3 | 51 |
| Example 15 | 1,3,5,2,4,6-Triazatriphosphorin hexachloride | 64.8 | 42 |

*Based on ammonia used.

The improvement in yield when using the catalyst of the invention is apparent from the data.

EXAMPLES 16 TO 19

So as to examine the effect of co-catalysts, into a mixture of acetone 50 g, methanol 9 g, cyanuric chloride 0.9 g and the co-catalyst shown in Table IV, 0.9 g ammonia gas was introduced over 4 hours at 10° to 15° C. 130 g Acetone then was added and the reaction mixture stirred for 10 hours at 50° to 55° C. The reaction mixture was worked up as in Examples 1 to 5. The results are shown in Table IV.

TABLE IV

| Example No. | Co-catalyst | Yield of Triacetone amine (g) | %* |
|---|---|---|---|
| Control 1 | Ammonium chloride 1.8 g (without cyanuric chloride) | 43.3 | 27 |
| Control 2 | None (with 1.8 g cyanuric chloride) | 60.6 | 38 |
| Example 16 | Ammonium chloride | 73.2 | 46 |
| Example 17 | Hydrazine dihydrochloride | 76.5 | 48 |
| Example 18 | Zinc chloride | 68.7 | 43 |
| Example 19 | Boron trifluoride (ether solution) | 70.8 | 44 |

*Based on acetone used.

The further improvement when a co-catalyst is used with the catalyst is apparent. The catalyst alone and co-catalyst alone (Controls 1 and 2) are not as effective, when used in the same total amount, as ½ the amount of each, used together, in the same total amount (Examples 16 to 19).

Having regard to the foregoing disclosure, the following is claimed as inventive and patentable embodiments thereof:

1. A process for the preparation of triacetone amine, which comprises reacting an acetone compound with ammonia at a temperature at which the reaction proceeds in the presence of a catalytically effective amount of a compound selected from the group consisting of organotin halides, 1,3,5,2,4,6-triazatriphosphorin hexahalides, and cyanuric halides until triacetone amine is formed, and then separating triacetone amine from the reaction mixture.

2. A process according to claim 1 in which the acetone compound is acetone or a condensation product of acetone with itself.

3. A process according to claim 2 in which the acetone condensation product is selected from the group consisting of diacetone alcohol, mesityl oxide and phorone.

4. A process according to claim 1 in which the organotin halide catalyst has the structure Rn Sn X$_{4-n}$ in which R is a hydrocarbon group selected from the group consisting of aliphatic hydrocarbon groups having from one to about ten carbon atoms and cycloaliphatic hydrocarbon groups having from five to about ten carbon atoms and such groups including oxy and ester groups in the chain;

X is halogen; and n is 1, 2 or 3.

5. A process according to claim 1 in which the 1,3,5,2,4,6-triaza-triphosphorinhexahalides have the formula:

wherein X is halogen, chlorine, bromine or iodine.

6. A process according to claim 1 in which the cyanuric halides have the formula:

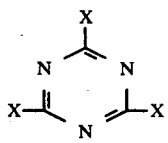

wherein X is halogen, chlorine, bromine or iodine.

7. A process according to claim 1 in which the amount of catalyst is within the range from about 0.01% to about 10% by weight of the acetone compound.

8. A process according to claim 1 in which there is combined with the catalyst a cocatalyst interacting beneficially to give synergistic results and selected from the group consisting of elemental bromine and elemental iodine; lithium, sodium and potassium bromide and iodide; ammonium chloride, bromide and iodide; hydrazine chloride; lithium and ammonium thiocyanate; maleic hydrazide, barium hydroxide; synthetic absorbents such as magnesium silicate hydrate and aluminum silicate hydrate; boron trifluoride, zinc chloride, and calcium chloride.

9. A process according to claim 8 in which the amount of co-catalyst is within the range from about 0.01 to about 10% by weight of the acetone compound.

10. A process according to claim 1 in which the molar ratio of acetone to ammonia is within the range from about 1:1 to about 20:1.

11. A process according to claim 1 in which the reaction temperature is within the range from about 0° C. and the boiling point of the reaction mixture at atmospheric pressure.

12. A process according to claim 11 in which the temperature is within the range from 30° to 60° C.

13. A process according to claim 1 in which the reaction temperature is within the range from 60° to 110° C. under a superatmospheric pressure up to 30 atmospheres.

14. A process according to claim 1 comprising an inert solvent boiling at a temperature of at least the selected reaction temperature.

15. A process according to claim 14 in which the solvent is selected from the group consisting of aliphatic hydrocarbons, aromatic hydrocarbons, chlorinated aliphatic and aromatic hydrocarbons, aliphatic and cycloaliphatic alcohols, and aliphatic and heterocyclic ethers.

16. A process according to claim 1 in which triacetone amine is recovered from the reaction mixture by distillation after adding an excess of strong aqueous alkali.

* * * * *